(12) United States Patent
Trotta

(10) Patent No.: US 6,547,768 B2
(45) Date of Patent: Apr. 15, 2003

(54) MEDICAL DEVICES WITH REDUCED FRICTION POLYAMIDES, AND METHOD

(75) Inventor: Thomas N. Trotta, Sunny Isles Beach, FL (US)

(73) Assignee: Cordis Corporation, Miami Lakes, FL (US)

( * ) Notice: Subject to any disclaimer, the term of this patent is extended or adjusted under 35 U.S.C. 154(b) by 98 days.

(21) Appl. No.: 09/736,776

(22) Filed: Dec. 14, 2000

(65) Prior Publication Data

US 2002/0077606 A1 Jun. 20, 2002

(51) Int. Cl.$^7$ .......................... A61M 25/00; A61M 5/00
(52) U.S. Cl. .................... 604/264; 264/512; 604/96.01
(58) Field of Search .......................... 604/103.5–103.9, 604/523–528, 264; 264/512, 563

(56) References Cited

U.S. PATENT DOCUMENTS

| | | | |
|---|---|---|---|
| 4,336,357 A | | 6/1982 | Bartoli et al. |
| 4,762,130 A | * | 8/1988 | Fogarty et al. .......... 128/348.1 |
| 4,898,591 A | | 2/1990 | Jang et al. |
| 5,258,160 A | | 11/1993 | Utsumi et al. |
| 5,344,400 A | * | 9/1994 | Kaneko et al. ................ 604/96 |
| 5,370,615 A | | 12/1994 | Johnson |
| 5,403,339 A | | 4/1995 | Nobuyoshi et al. |
| 5,433,713 A | * | 7/1995 | Trotta ........................ 604/264 |
| 5,538,510 A | * | 7/1996 | Fontirroche et al. ........ 604/256 |
| 5,797,948 A | * | 8/1998 | Dunham ..................... 606/194 |
| 5,814,384 A | | 9/1998 | Akkapeddi et al. |
| 5,820,594 A | | 10/1998 | Fontirroche et al. |
| 5,849,846 A | * | 12/1998 | Chen et al. ................. 525/166 |
| 5,921,957 A | | 7/1999 | Killion et al. |
| 5,947,925 A | | 9/1999 | Ashiya et al. |
| 6,033,380 A | * | 3/2000 | Butaric et al. ................ 604/96 |
| 6,036,670 A | | 3/2000 | Wijeratne et al. |
| 6,086,970 A | * | 7/2000 | Ren ........................... 428/36.9 |
| 6,093,463 A | * | 7/2000 | Thakrar ..................... 428/36.9 |
| 6,159,187 A | | 12/2000 | Park et al. |
| 6,159,227 A | * | 12/2000 | Di Caprio et al. .......... 606/192 |
| 6,165,166 A | * | 12/2000 | Samuelson et al. ......... 604/524 |
| 6,200,290 B1 | | 3/2001 | Burgmeier |
| 6,280,434 B1 | | 8/2001 | Kinoshita et al. |
| 6,325,790 B1 | | 12/2001 | Trotta |
| 6,428,552 B1 | | 8/2002 | Sparks |

OTHER PUBLICATIONS

A. D. Jenkins (UK), et al., "Glossary Of Basic Terms In Polymer Science"; International Union Of Pure And Applied Chemistry Macromolecular Division Commission On Macromolecular Nomenclature, *Pure Appl. Chem.,* vol. No. 68, 8, 5 page excerpt,1996. © 1996 IUPAC.

* cited by examiner

Primary Examiner—Charles G. Freay
Assistant Examiner—Han L. Liu
(74) Attorney, Agent, or Firm—Michael W. Montgomery

(57) ABSTRACT

The medical devices of the present invention include polymer blends of polyamide and maleated polyethylene. The polyamide component of the blended materials of the present invention may include both homopolymers and copolymers. The other component of the present invention is preferably HDPE, with the addition of maleic anhydride. Accordingly, the materials of the present invention provide a unique combination of physical properties that are advantageous for use in various devices, including medical devices for maneuvering through the circulatory system. The properties of high-strength, capability of bonding to other polyamides, and kink resistance are retained. In addition, several physical properties and benefits are provided by the materials of the present invention, including low friction, functional groups to bond to low friction services, a range of flexibilities, and low gel counts.

19 Claims, 5 Drawing Sheets

MEDICAL DEVICES WITH REDUCED FRICTION POLYAMIDES, AND METHOD

BACKGROUND AND SUMMARY OF THE INVENTION

1. Technical Background

The present invention relates generally to materials and methods for medical devices.

2. Discussion

A variety of polymers are used to make many different medical devices, including catheters, sheaths, grafts, balloons, catheter sheath introducers, and other medical devices used in the body of a patient. Such polymers used for medical devices include nylons, polyethylenes, polyesters, polyurethanes, and polyamides.

Several desirable features for such polymers include in particular flexibility and low friction, as well as strength, the capability of being produced in a range of different flexibilities, and column stiffness.

Of the polyamide materials, polyamide-12 in the form of a homopolymer has been used for a variety of medical devices, some types of which are referred to as nylon-12. Another material in the polyamide family that has been used includes polyamide-12 in a copolymer with other materials, including polyether block amide (PEBA). Also, polyamide-12 may be blended with PEBA to produce a material having a desired flexibility for a given application. However, PEBA generally has physical properties that are less than optimal for certain applications, including relatively high friction, a relatively high level of gels, and the absence of amide functional groups when the material is made with relatively high flexibility or low durometers.

Another example is polyamide made in a coextrusion with high-density polyethylene (HDPE), which results in a multiple layer device. U.S. Pat. No. 5,538,510 describes multi-layer coextrusions of polyamides with high-density polyethylene. The resulting structure has relatively low friction on the high-density polyethylene layer, while the polyamide layer can be bonded to other polyamide materials by application of heat and pressure. It is desirable to develop such a material having these properties that is available for certain applications in a selective range of flexibilities.

The materials of the present invention provide a unique combination of physical properties that are advantageous for use in medical devices for maneuvering through the circulatory system. The properties of high-strength, capability of bonding to other polyamides, and kink resistance are retained. In addition, several physical properties and benefits are provided by the materials of the present invention, including low friction, functional groups to bond to low friction surfaces, a range of flexibilities, and low gel counts.

Accordingly, the materials of the present invention preferably include blends of polyamide and maleated polyethylene. The polyamide component of the blended materials of the present invention may of course include both homopolymers and copolymers, of which the copolymer is preferred.

More particularly, this copolymer preferably uses disruption of the crystallinity of the polyamide to increase flexibility to a desired level. This method of increasing flexibility is in contrast to and more effective than PEBA, for example, which is also a copolymer. Instead of crystalline disruption, PEBA uses flexible linkages for flexibility.

The other component of the polymers of the present invention, maleated polyethylene, is preferably HDPE, with the addition of the maleic anhydride.

Preferably, the polyethylene component of the blended polymers of the present invention is as described in U.S. Pat. No. 5,538,510, entitled "Catheter Having Coextruded Tubing," issued to Fontirroche, et al. on Jul. 23, 1996, which is incorporated by reference. More specifically, the preferred polyethylene component of the blended polymer materials of the present invention is high-density polyethylene modified with maleic anhydride.

As an example, the present invention will be described in relation to medical devices, and more particularly to medical catheters. However, it should be understood that the present invention relates to any apparatus or method having the features of the present invention, and is not limited to a particular material or type of design.

These and various other objects, advantages and features of the invention will become apparent from the following description and claims, when considered in conjunction with the appended drawings.

DETAILED DESCRIPTION OF THE PREFERRED EMBODIMENT

Figure 1:
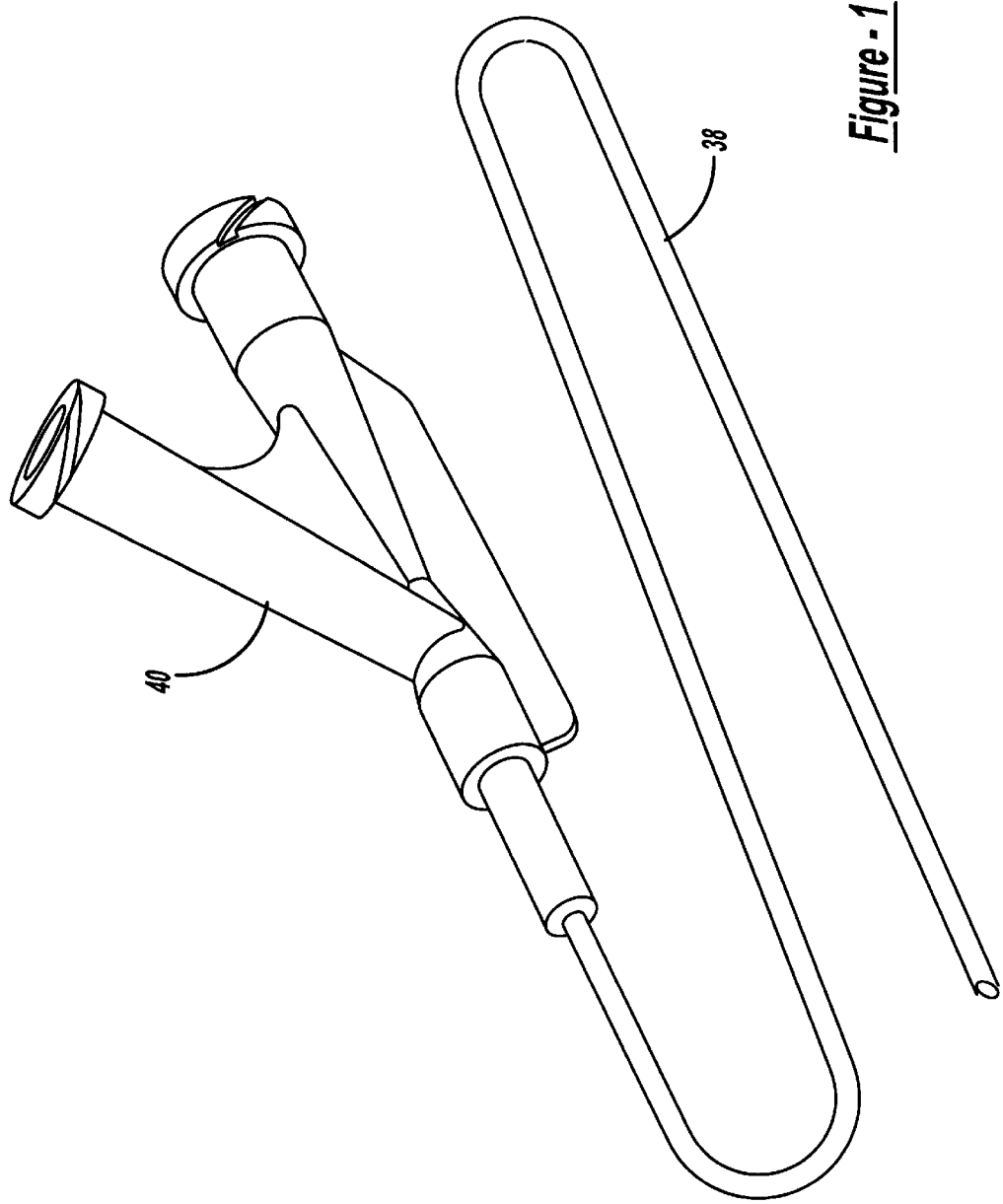
FIG. 1 is an external perspective view of a catheter, arranged according to the principles of the present invention.
Figure 2:
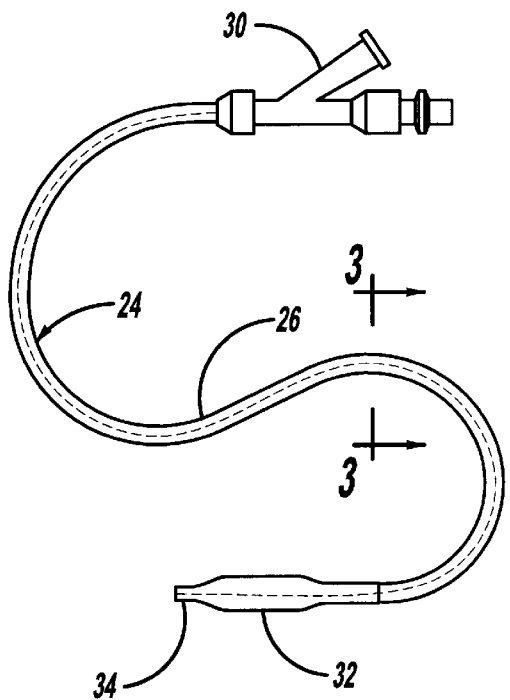
FIG. 2 is an external perspective view of a balloon catheter, arranged according to the principles of the present invention.
Figure 3:
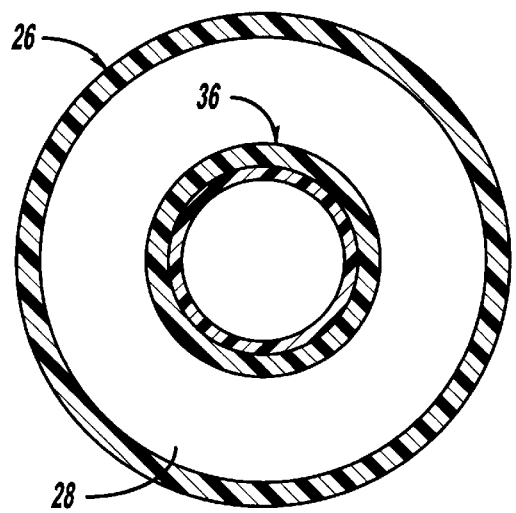
FIG. 3 is a transverse cross-sectional view of the balloon catheter of FIG. 2, taken along line 3—3.
Figure 5:
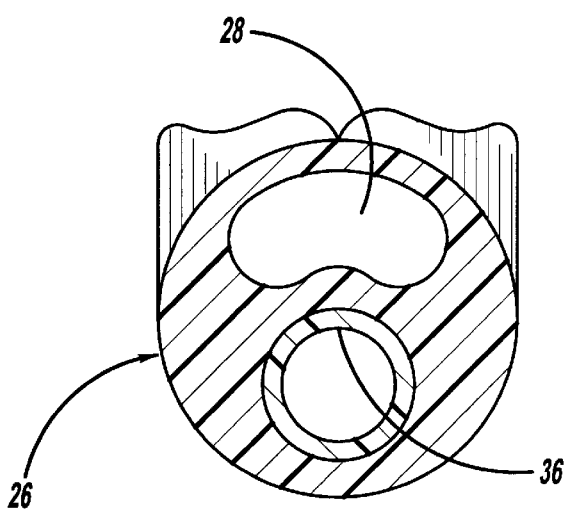
FIG. 5 is a transverse cross-sectional view of the balloon catheter of FIG. 4, taken along line 5—5.
Figure 4:
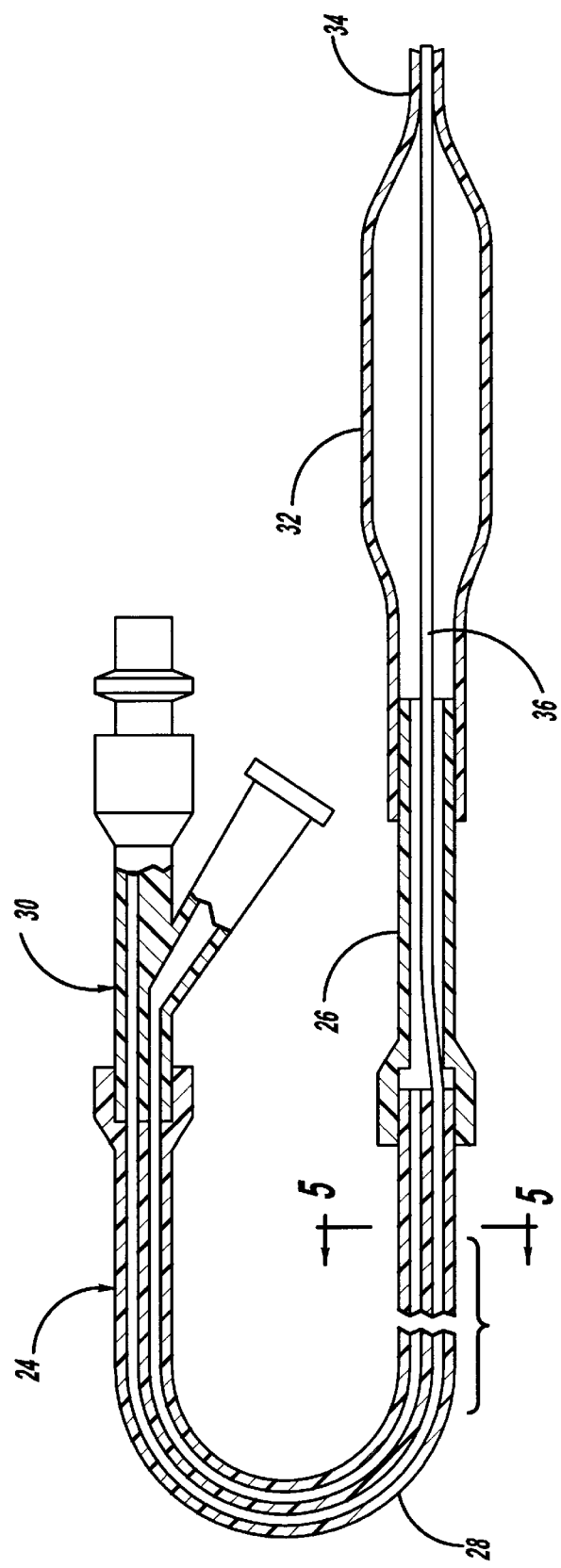
FIG. 4 is a longitudinal cross-sectional view of a balloon catheter, arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, several aspects of the present invention are depicted, with several of the preferred embodiments of the present invention being shown. The illustrated catheters are of course only examples of some of many different medical devices using the novel polymers within the scope of the present invention.

The medical devices of the present invention incorporate a unique family of polymers including a polymer blend of polyamide and maleated polyethylene. These novel polymer blends present several advantageous features for medical devices, including flexibility and low friction, as well as strength, column stiffness, and the capability of being produced in a range of different flexibilities.

The polyamide component of the blended materials of the present invention may of course include both homopolymers and copolymers, of which the copolymer is preferred. The other component of the present invention is preferably HDPE, with the addition of the maleic anhydride.

A primary advantage of the present invention is the novel and unique combination of the following properties: flexibility, lubricity, and the compatibility of the various polymer constituents of the materials of the present invention. The term compatibility generally refers to the tendency of different polymer constituents to bond or heat-fuse with each other.

Another primary advantage is increased lubricity, when compared with other flexible polyamides, and in particular when compared with PEBA.

EXAMPLE 1

Centering Balloon Catheter

The blended polymer materials of the present invention may be used to construct a centering balloon catheter for intravascular radiation therapy, which may be similar to that shown in FIGS. 6–10. The centering balloon catheter 10 may generally include a flexible catheter shaft 12 defining an inflation lumen 14, a proximal hub 16, and a centering balloon 18 at the distal end 20 of the catheter 10. The uniform effective radius of the centering balloon 18 provides the centering effect.

Many variations and other features are known in the art, including various polymer and metal materials, a guidewire lumen in a rapid-exchange or over-the-wire configuration, the catheter shaft having at least a portion made of metal hypotube, or the catheter shaft defining a single lumen, dual lumen or with a coaxial arrangement, etc. Another possible arrangement is to form a multiple layer balloon, with one of the layers being a blended polymer material of the present invention.

Figure 6:
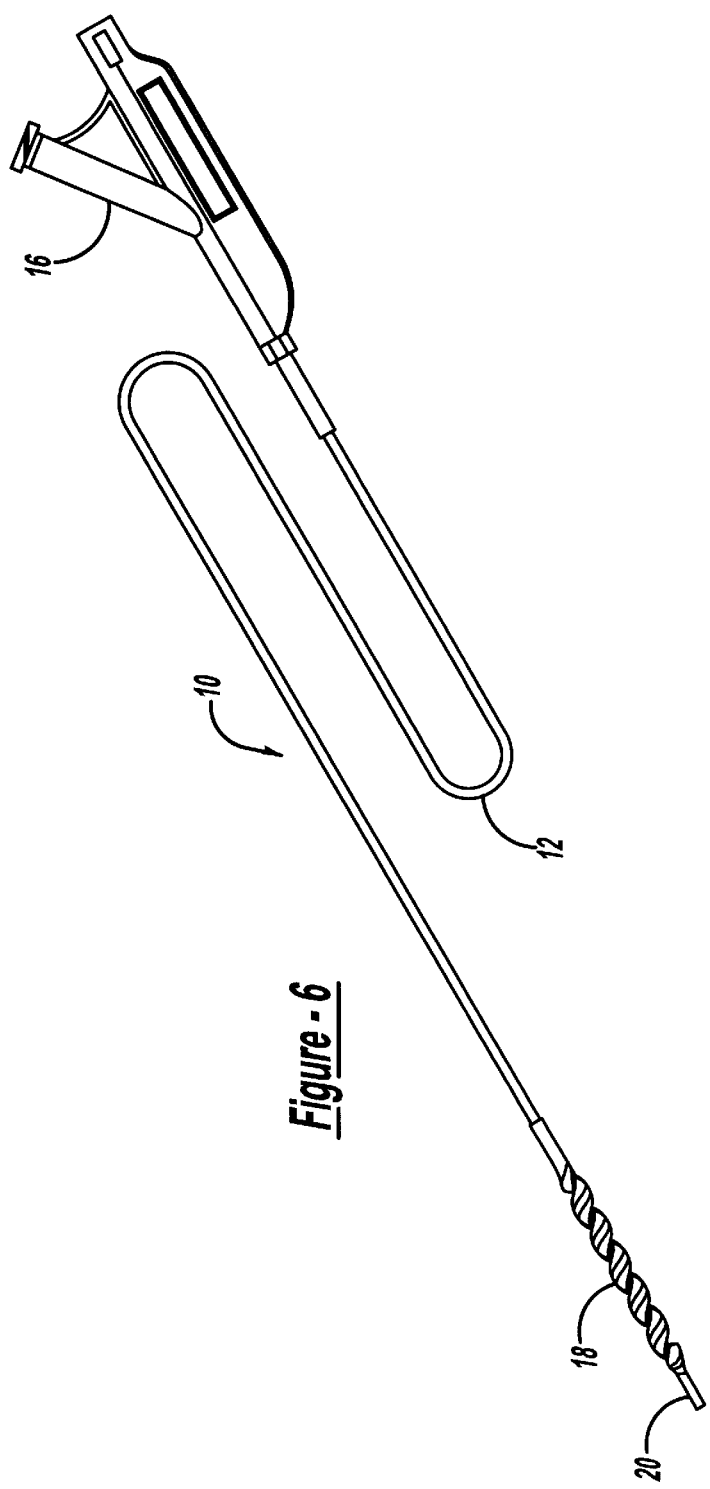
FIG. 6 is an external perspective view of a centering balloon catheter, arranged according to the principles of the present invention.
Figure 7:
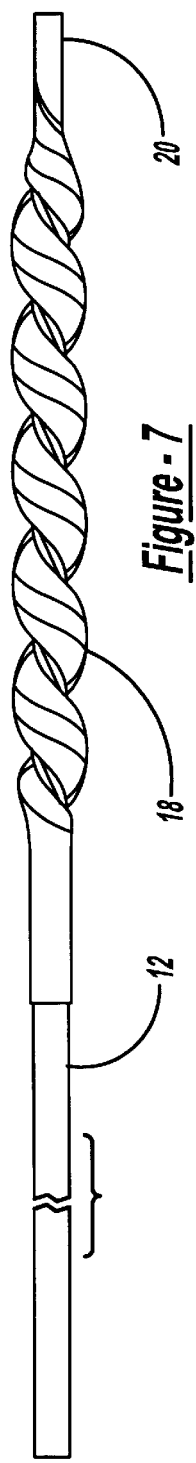
FIG. 7 is a partial elevational view of a portion of the centering balloon catheter of FIG. 6.
Figure 8:
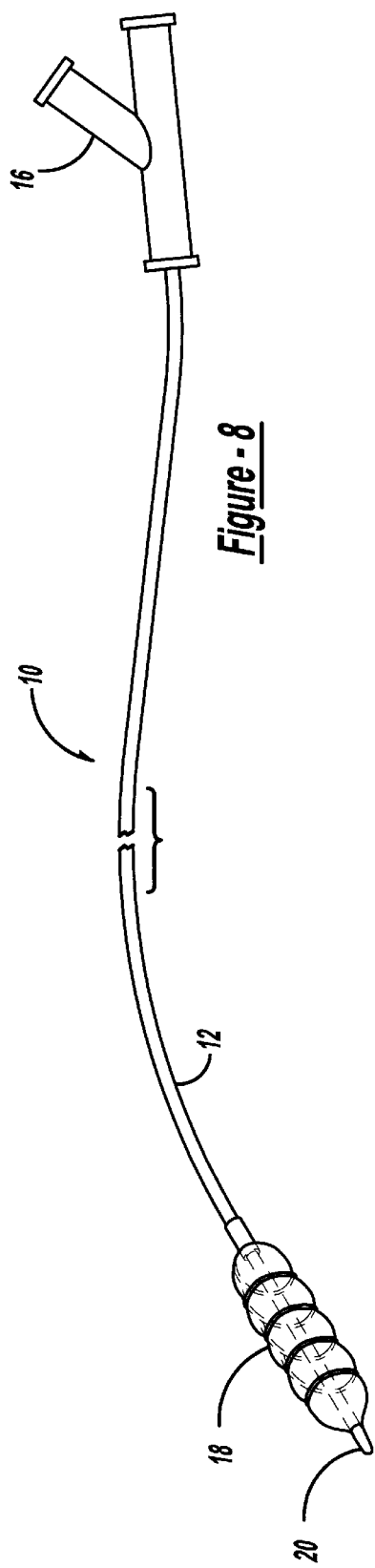
FIG. 8 is an external perspective view of a centering balloon catheter according to the present invention.
Figure 9:
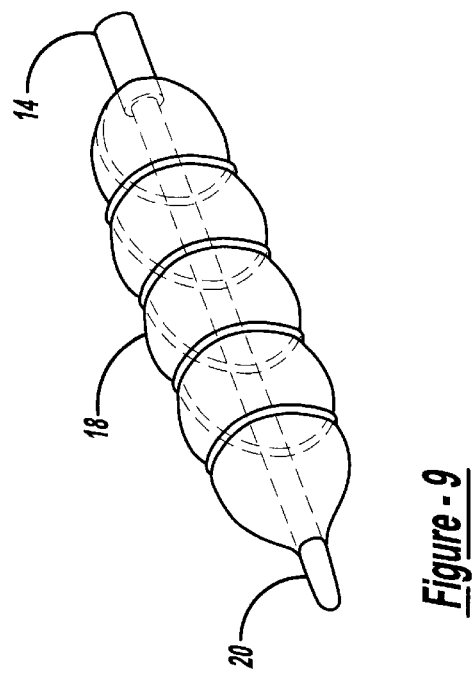
FIGS. 9 and 10 are partial views of a portion of the centering balloon catheter of FIG. 8.
Figure 10:
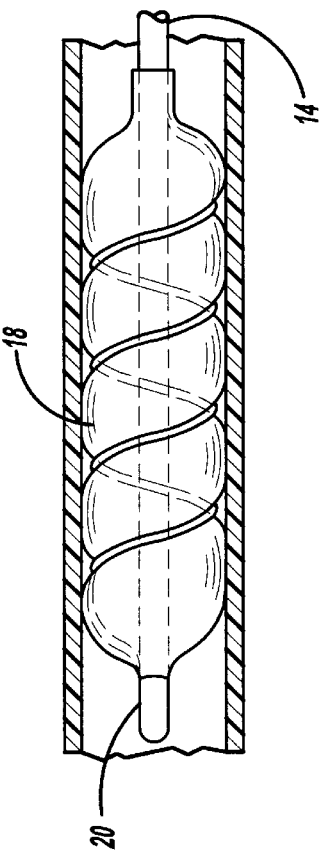

It is also desirable to allow blood flow or perfusion between positions proximal and distal of the balloon, even while the balloon is inflated. A possible design for allowing such blood flow is to form the balloon in a spiral shape, as illustrated in FIG. 6. In such a spiral design, the smallest diameter portion of the spiral balloon is slightly larger than the outer diameter of the catheter shaft, yet the largest diameter portion of the spiral balloon 18 is large enough to contact the blood vessel wall. When inflated, the resulting spiral channel will tend to allow blood flow in a spiral path from a position upstream of the balloon to a position downstream.

Other possible configurations for enabling perfusion of blood past the inflated balloon include a straight or contoured groove or channel, or an annular balloon shape, or a perfusion lumen defined by at least a portion of the catheter shaft.

It is therefore desirable for a centering balloon to have the following physical properties: relatively high flexibility; relatively low friction; capable of maintaining the desired spiral configuration when the balloon is pressurized; capable of being heat-bonded to the catheter shaft; and a tendency for the folds of the pleated balloon to refrain from sticking to each other, or tacking, during the processes of sterilization, shipping, or storage.

Depending upon the employed use, the blended materials of the present invention can successfully meet all of these specifications and properties. In this Example, centering balloons were made according to the following formula: 45 percent Rilsan® 67.33, 45 percent Grilamid® CF62BSE, and 10 percent Plexar® PX-209. These materials are available from the following suppliers: Rilsan from Atofina Chemicals in Philadelphia, Pa.; Grilamid from EMS-CHEMIE in Charlotte, N.C. and Plexar from Equistar in Houston, Tex.

This blended polymer made according to the principles of the present invention was tested and found to perform better than other commonly used polyamides and polyethylene. When formed into a balloon, the material is stronger, has a lower coefficient of friction, and a better spiral shape memory than polyethylene, PEBA, and has a flexibility similar to either of the copolyamides used to make the blended material.

The melting temperatures of each constituent of a polymer of the present invention, Rilsan, Grilamid, and Plexar for example, are believed to preferably be selected within approximately 30° C. of each other.

EXAMPLE 2

Balloon Catheter Shaft

A catheter shaft can be enhanced by using the blended polymer materials of the present invention. One particular example is a balloon catheter for intravascular angioplasty, which may be similar to that shown in FIGS. 2–5. The balloon catheter 24 may generally include a flexible catheter shaft 26 defining an inflation lumen 28, a proximal hub 30, and a balloon 32 at the distal end 34 of the catheter. As with the centering balloon catheter described above, many variations and other features are known in the art.

A tubular inner body or guidewire tube 36 of a catheter shaft can be enhanced by using the blended polymer materials of the present invention, because it is desirable to form a tubular inner body or guidewire tube 36 of greater flexibility than is possible from a polyamide homopolymer alone. Moreover, the blended polymer materials of the present invention tend to exhibit less friction and more lubricity when advancing or withdrawing the catheter in a body passage, or when advancing or withdrawing a guidewire in a guidewire lumen defined by the catheter shaft.

Many variations are of course also possible, including forming a single lumen or multiple lumen shaft member of the.blended polymer materials of the present invention. Another possible arrangement is combining a first shaft member made of a blended polymer material of the present invention with a second shaft member, perhaps made of another polymer or metal material. Yet another possible arrangement is to form a shaft member as a coextrusion of a blended polymer material of the present invention with another material.

The materials and constituents of the present invention used for this Example of a balloon catheter shaft may of course preferably have the same features, specifications and properties, as the constituents from the same suppliers as in the first Example.

EXAMPLE 3

Microcatheters

The blended polymers of the present invention may also be used in small, relatively thin-walled interventional and diagnostic catheters called microcatheters, which may generally be used in neurological applications. Generally, such a microcatheter may be similar to that shown in FIG. 1, having a flexible catheter shaft 38 and a proximal hub 40. A relatively short distal segment of these catheters are preferably extremely flexible, and they are often guided through another larger catheter along a majority of the desired vascular path.

It is desirable to provide such a microcatheter having a relatively low coefficient of friction, because many of the larger catheters may be made with materials having relatively high friction. Accordingly, it is desirable to form all or a portion of the shaft of a microcatheter of the blended polymer materials of the present invention.

Of course, many variations are also possible, including forming a microcatheter shaft member as a coextrusion of a blended polymer material of the present invention with another material.

The materials and constituents of the present invention used for this Example of a microcatheter may of course preferably have the same features, specifications and properties, as the constituents from the same suppliers as in the first Example.

It should be understood that an unlimited number of configurations for the present invention could be realized. -The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A balloon catheter, comprising:
   a catheter shaft having a proximal and distal end, defining an inflation lumen;
   a polymer balloon affixed to the catheter shaft near the distal end, the inflation lumen communicating with an interior of the balloon; and
   at least a portion of the shaft being made of a polymer blend of polyamide and maleated polyethylene.

2. The balloon catheter of claim 1, further comprising a guidewire lumen defined by and extending through at least a portion of the catheter shaft, the guidewire lumen having an inner wall surface being made of said polymer blend.

3. The balloon catheter of claim 1, wherein at least a portion of the catheter shaft is formed of a multiple layer tube, at least one of the layers being made of said polymer blend.

4. The balloon catheter of claim 1, wherein the balloon is an angioplasty balloon.

5. The balloon catheter of claim 1, further comprising a source-wire lumen defined by and extending through at least a portion of the catheter shaft, the source-wire lumen having a closed distal end near a distal end of the catheter; such that the balloon when inflated will tend to center the source-wire lumen distal end within a patient's body passage.

6. The balloon catheter of claim 1, wherein the polyamide component of the polymer blend is a homopolymer.

7. The balloon catheter of claim 1, wherein the polyamide component of the polymer blend is a copolymer.

8. The balloon catheter of claim 1, wherein the maleated polyethylene component of the polymer blend is a homopolymer with maleic anhydride.

9. The balloon catheter of claim 1, wherein the maleated polyethylene component of the polymer blend is HDPE with maleic anhydride.

10. A centering balloon catheter, comprising:
    a catheter shaft having a proximal and distal end, defining an inflation lumen;
    a polymer balloon affixed to the catheter shaft near the distal end, the inflation lumen communicating with an interior of the balloon; and
    a source-wire lumen defined by and extending through at least a portion of the catheter shaft, the source-wire lumen having a closed distal end at a position inside the balloon; such that the balloon when inflated.will tend to center the source-wire lumen distal end within a patient's body passage; wherein
    at least a portion of the balloon is made of a polymer blend of polyamide and maleated polyethylene.

11. The centering balloon catheter of claim 10, wherein the balloon has a spiral shape to define an external spiral channel for allowing blood to perfuse past the balloon in its inflated state.

12. A medical device made of a polymer material, comprising a polymer blend of polyamide and maleated polyethylene.

13. A catheter, comprising a shaft member, at least a portion of the shaft member being made of a blend of polyamide and maleated polyethylene.

14. A polymer material for use in a medical device, comprising: a blend of polyamide and maleated polyethylene.

15. The polymer material of claim 13, having the physical properties of relatively high strength, relatively low friction, and the capability of bonding to polyamide materials.

16. The polymer material of claim 13, having functional groups capable of bonding to low friction surfaces.

17. The polymer material of claim 13, wherein the polyamide component of the blended polymer material is a homopolymer.

18. The polymer material of claim 13, wherein the polyamide component of the blended polymer material is a copolymer.

19. The polymer material of claim 13, wherein the maleated polyethylene component of the blended polymer material is HDPE with maleic anhydride.

* * * * *